United States Patent
Shultz

(10) Patent No.: US 6,702,951 B2
(45) Date of Patent: Mar. 9, 2004

(54) SCENT ADSORBING LIQUID FORMULATION

(75) Inventor: Scott S. Shultz, Cannon Falls, MN (US)

(73) Assignee: Robinson Laboratories, Inc., Cannon Falls, MN (US)

( * ) Notice: Subject to any disclaimer, the term of this patent is extended or adjusted under 35 U.S.C. 154(b) by 0 days.

(21) Appl. No.: 09/905,251

(22) Filed: Jul. 13, 2001

(65) Prior Publication Data

US 2002/0100893 A1 Aug. 1, 2002

Related U.S. Application Data

(60) Provisional application No. 60/238,668, filed on Oct. 6, 2000.

(51) Int. Cl.⁷ .......................... A61L 2/00; A61L 101/04; D06M 11/00
(52) U.S. Cl. .................... 252/8.91; 424/76.1; 424/76.2; 424/76.21; 424/76.8; 510/513; 512/7; 422/5
(58) Field of Search ....................... 252/8.91; 424/76.1, 424/76.2, 76.21, 76.8; 510/513; 512/7; 422/5

(56) References Cited

U.S. PATENT DOCUMENTS

| | | | | |
|---|---|---|---|---|
| 2,984,584 A | | 5/1961 | Glarum et al. ................. 117/76 |
| 3,783,085 A | | 1/1974 | Pearson et al. ................ 161/87 |
| 4,181,712 A | | 1/1980 | Rialdi | |
| 4,510,193 A | | 4/1985 | Blücher et al. | |
| 4,833,181 A | | 5/1989 | Narukawa et al. | |
| 4,837,020 A | | 6/1989 | Mise et al. .................... 424/68 |
| 4,909,986 A | * | 3/1990 | Kobayashi et al. ............. 422/4 |
| 4,946,672 A | | 8/1990 | Gibbs ......................... 424/76.1 |
| 5,197,208 A | | 3/1993 | Lapidus | |
| 5,238,899 A | | 8/1993 | Kadowaki et al. ............ 502/401 |
| 5,383,236 A | | 1/1995 | Sesselmann | |
| 5,534,165 A | * | 7/1996 | Pilosof et al. ............... 252/8.91 |
| 5,539,930 A | | 7/1996 | Sesselmann | |
| 5,585,107 A | | 12/1996 | Vickers | |
| 5,593,670 A | | 1/1997 | Trinh et al. | |
| 5,714,137 A | * | 2/1998 | Trinh et al. ................. 424/76.4 |
| 5,776,378 A | * | 7/1998 | Knight ......................... 261/30 |
| 5,780,020 A | | 7/1998 | Peterson et al. | |
| 5,790,987 A | | 8/1998 | Sesselmann | |
| 5,858,335 A | | 1/1999 | Lucas et al. .................... 424/65 |
| 5,861,143 A | | 1/1999 | Peterson et al. ............... 424/65 |
| 5,861,144 A | | 1/1999 | Peterson et al. | |
| 5,861,145 A | | 1/1999 | Lucas et al. .................... 424/65 |
| 5,871,718 A | | 2/1999 | Lucas et al. .................... 424/65 |
| 5,871,719 A | | 2/1999 | Lucas et al. .................... 424/65 |
| 5,874,067 A | | 2/1999 | Lucas et al. .................... 424/65 |
| 5,882,638 A | | 3/1999 | Dodd et al. | |
| 5,885,599 A | * | 3/1999 | Peterson et al. .............. 424/405 |
| 5,891,391 A | * | 4/1999 | Fore ............................... 422/5 |
| 5,897,854 A | | 4/1999 | Lucas et al. .................... 424/65 |
| 5,897,855 A | | 4/1999 | Trinh et al. .................... 424/65 |
| 5,928,631 A | | 7/1999 | Lucas et al. .................... 424/65 |
| 5,942,214 A | | 8/1999 | Lucas et al. .................... 424/65 |
| 6,009,559 A | * | 1/2000 | Sesselmann ................. 2/243.1 |
| 6,057,262 A | | 5/2000 | Derbyshire et al. | |
| 6,061,384 A | | 5/2000 | Koslow | |
| 6,100,233 A | | 8/2000 | Sivik et al. | |
| 6,114,280 A | | 9/2000 | Stephens | |
| 6,129,892 A | | 10/2000 | Garrett ............................ 422/5 |
| 6,183,766 B1 | | 2/2001 | Sine et al. .................... 424/405 |
| 6,340,447 B2 | * | 1/2002 | Johnson .......................... 422/5 |
| 6,440,415 B1 | * | 8/2002 | Johnson ........................ 424/125 |
| 6,491,840 B1 | * | 12/2002 | Frankenbach et al. ...... 252/8.91 |
| 6,497,862 B2 | * | 12/2002 | Oku et al. ...................... 424/65 |

FOREIGN PATENT DOCUMENTS

| EP | 0 144 553 | 6/1985 |
| EP | 0 392 528 | 10/1990 |

OTHER PUBLICATIONS

Military Specification MIL–C–43858B, *Cloth, Laminated, Nylon Tricot Knit, Polyurethane Foam Laminate, Chemical Protective and Flame Resistant*, Jan. 16, 1986.

* cited by examiner

*Primary Examiner*—Anthony J. Green
(74) *Attorney, Agent, or Firm*—Patterson, Thuente, Skaar and Christensen, P.A.

(57) ABSTRACT

An odor-absorbing liquid formulation, one embodiment thereof comprising a preservative, an alkali metal salt, and a particulate odor-adsorbing agent such as activated carbon. The formulation may further include an alkylaryl polyether nonionic surfactant and may have an alkaline pH. The present liquid formulation is applied to apparel to be worn during hunting or observation to avoid being sensed by animals.

43 Claims, No Drawings

SCENT ADSORBING LIQUID FORMULATION

CROSS-REFERENCES TO RELATED APPLICATIONS

This application claims priority under 35 U.S.C. § 119 (e) to, and hereby incorporates by reference, U.S. Provisional Application No. 60/238,668, filed Oct. 6, 2000.

BACKGROUND OF THE INVENTION

1. Field of the Invention

This invention is directed to substances for suppressing scents. More particularly, this invention is directed to liquid formulations applied to articles of attire, footwear, and equipment to prevent a person's scent from emanating therefrom.

2. Background of the Invention

It is unavoidable that persons generate and give off odors (or scents). These odors may originate from sources such as natural body secretions (perspiration, oils), bacteria residing on the skin, and clothing worn by the individual.

Many animals, such as bear, deer, elk, and fox, have highly developed abilities to detect a person in proximity by sensing the person's odor. Therefore, persons hunting and observing these animals, in addition to visual camouflage, often attempt to prevent these animals from sensing odors characteristic of humans. To this end, several liquid and cream formulations are applied to the user's skin for masking or camouflaging the person's scent. Other substances are applied during bathing to temporarily remove the user's scent. Liquid formulations are also applied to garments worn by these persons to reduce odors. These liquid formulations have been proven to be effective in preventing the user's body odor from being detected by game. These liquid formulations typically contain ingredients for preventing or minimizing formation of odor causing chemical compounds. However, a liquid formulation suitable to be applied to clothing, footwear, and equipment with longer lasting and even more effective odor-suppressing properties would be even more desirable. There then is a need for a long lasting, odor-suppressing liquid formulation, which can be applied to apparel worn when hunting or observing animals and which can suppress odors caused by chemical compounds already present.

SUMMARY OF THE INVENTION

This invention substantially meets the aforementioned needs of the industry by providing a liquid formulation suitable to be applied to an article of apparel, the article of apparel to be worn by, or to be in close contact with, a person hunting or observing game or otherwise used to prevent game from sensing the user's scent. The present liquid formulation may also be advantageously applied to articles of equipment and with beneficial effects similar to those effects encountered when used on articles of apparel. When the present liquid formulation is applied to textiles and other materials used in making apparel, game animals are much less likely to detect the user. One way in which these odors are suppressed is by adsorbing odor-producing substances. Moreover, the liquid formulation of this invention may contain a substance which inhibits odiferous substance formation.

One embodiment of the present scent-adsorbing liquid formulation includes an alkali metal carbonate or bicarbonate salt, and a particulate, odor-adsorbing agent such as activated carbon. In another embodiment, a preservative may be included. The preservative may include a substance with antimicrobial activity. A nonionic surfactant, such as an alkylaryl polyether alcohol, may also be present in an amount sufficient to allow the preservative to be incorporated into the formulation as a solution, suspension, or emulsion and/or to allow for better coverage when applied to the article of apparel. The liquid formulation may further include a base, such as an alkali metal hydroxide, in an amount sufficient to provide a formulation pH between about 9 and 11. An alkaline pH may be advantageous in promoting penetration or coverage of the substance being treated, in retarding formation of some odiferous substances per se, and in providing an environment in which the preservatives are most effective in inhibiting bacterial (or generally microfloral) growth and development.

It is one feature that the present liquid formulation suppresses odors otherwise emanating from users by providing an adsorptive agent, such as particulate activated carbon. The liquid formulation is applied to an article of attire or other object worn by, or in close contact with, the user. The adsorptive agent adsorbs odiferous substances given off by the user which otherwise become airborne and would be detected by animals.

It is a second feature of this invention that some embodiments of the present liquid formulation may also inhibit or retard generation of odiferous substances by containing a preservative, such as an antimicrobial agent. The preservative, when applied to an item of apparel or an article to be in close contact with a user, stops or inhibits microflora (such as bacteria) from producing odiferous substances, which might otherwise be detected by animals.

It is a third feature of this invention that the present liquid formulation can be applied to garments worn by a user while hunting or observing game animals. When garments to which the present liquid formulation is applied are worn, the likelihood of being scented by the game animals is minimized. Stated otherwise, the likelihood of game animals moving into near proximity with the wearer of apparel treated by the present liquid formulation is maximized because of eliminated or greatly reduced odors emanating from the wearer.

Additional objects, advantages, and features of various embodiments of this invention will be set forth in part in the description which follows, and in part will become apparent to those skilled in the art. The objects and advantages of various embodiments of this invention may be realized and attained by persons of ordinary skill in the art by means of the instrumentalities and combinations particularly pointed out in the description below.

DETAILED DESCRIPTION OF THE INVENTION

The present invention is a substantially liquid formulation suitable to be applied to fabrics or other articles of apparel, footwear, and items of equipment. These articles, when the present liquid formulation has been applied thereto, effectively prevent game animals from detecting a wearer's body odor or scent.

The term "substantially liquid formulation" is contemplated to describe formulations which may contain nonliquid ingredients, but can nonetheless be applied by methods used to apply other liquids after the nonliquid ingredients are suspended, e.g., by agitation. One such method of application is by using a spray bottle.

The present invention may include an odor-adsorbing material, the odor-adsorbing material suspendable (or otherwise included) in an aqueous solution (or emulsion). The present formulation may also include one or more preservatives (to include one or more antimicrobial formulations), an alkali metal carbonate or bicarbonate, one or more surfactants, and/or an alkali metal hydroxide. Powdered activated carbon may be advantageously suspended in this liquid formulation. Optionally, a dye is included. Unless otherwise specified, ingredient proportions are stated in percent by weight of the final product.

Preservatives

Suitable preservatives for use in the present formulation include:

1. Alkali metal salts of $C_2$–$C_6$ carboxylic acids, e.g., sodium propionate (Niacet Corporation).
2. Derivatives of imidazoles, e.g., imidazolidinyl urea (Tristad 1U, Tri-K Industries).
3. Mixtures of esterified phenols and phenol derivatives, e.g., methylparaben, propylparaben, and diazolidinyl urea (Germaben 2, Sutton Labs).
4. Organic sulfur compounds.
   a. 3-isothiazolones and salts formed by reactions with acids such as hydrochloric, nitric, and sulfuric acids; e.g., 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; 5-chloro-2-methyl-3-isothiazolone; 2-methyl-4-isothiazolin-3-one; and mixtures thereof. An exemplary broad spectrum 3-isothiazolone preservative is available as Kathon® CG by Rohm and Haas Company.
   b. Sodium pyrithione and mixtures of organic sulfur compounds.
5. Halogenated compounds.
   a. 5-bromo-5-nitro-1,3-dioxane (e.g., Bronidox L® from Henkel).
   b. 2-bromo-2-nitropropane-1,3-diol, (e.g., Bronopol® from Inolex).
   c. 1,1'-hexamethylene bis(5-(p-chlorophenyl) biguanide), commonly known as chlorhexidine and its salts.
   d. 1,1,1-trichloro-2-methylpropan-2-ol, commonly known as chlorobutanol.
   e. 4,4'-(trimethylenedioxy)bis-(3-bromobenzamidine) diisethionate or dibromopropamidine.
6. Cyclic organic nitrogen compounds.
   a. Imidazolidinedione compounds.
      i. 1,3-bis(hydroxymethyl)-5,5-dimethyl-2,4-imidazolidinedione, commonly known as dimethyloldimethylhydantoin, or DMDM hydantoin, available as, e.g., Glydant® from Lonza.
      ii. N-[1,3-bis(hydroxymethyl)2,5-dioxo-4-imidazolidinyl]-N,N'-bis(hydroxymethyl) urea, commonly known as diazolidinyl urea, available under the trade name Germall II® from Sutton Laboratories, Inc.
      iii. N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115®.
   b. Polymethoxy Bicyclic Oxazolidine, such as Nuosept® C from Huls America.
7. Low Molecular Weight Aldehydes.
   a. Formaldehyde.
   b. Glutaraldehyde.
8. Cationic and/or Quaternary Compounds.
   a. Polyaminopropyl biguanide, also known as polyhexamethylene biguanide, such as Cosmocil CQ® from ICI Americas, Inc., or Mikrokill® from Brooks, Inc.
   b. 1-(3-Chlorallyl)-3,5,7-triaza-1-azoniaadamantane chloride, available, e.g., Dowicil 200 from Dow Chemical.
9. Dehydroacetic Acid.
10. Phenyl and Phenoxy Compounds. Some non-limiting examples of phenyl and phenoxy compounds suitable for use in the present invention are:
    a. 4,4'-diamidino-.alpha.,.omega.-diphenoxypropane diisethionate, commonly known as propamidine isethionate.
    b. Benzyl alcohol.
    c. 2-phenylethanol.
    d. 2-phenoxyethanol.

The preservative or preservatives may be present in an amount between about 0.025% and 5%, 0.025% and 2.5%, 0.025% and 1%, or any range subsumed therein.

Surfactants

A variety of surfactants may be useful in the present invention. These surfactants are contemplated to include nonionic, anionic, and/or cationic surfactants. These surfactants may facilitate the inclusion of other substances in the present formulation as solutions, dispersions, and/or emulsions. These surfactants may also enable more complete coverage when the present formulation is applied to articles of attire.

Nonlimiting examples of nonionic surfactants which may be suitable for use in embodiments of this invention are recited below.

1. Nonylphenol ethoxylates with 4–100 ethylene oxide groups per nonylphenol molecule.
2. Dinonylphenol ethoxylates with 4–150 ethylene oxide groups per dinonylphenol molecule.
3. Linear alcohol ethoxylates with the alcohol chain consisting of 2–24 carbon atoms and with 2 to 150 ethylene oxide groups per alcohol molecule.
4. Dodecylphenol ethoxylates with 4–100 ethylene oxide groups per dodecylphenol molecule.
5. Octylphenol ethoxylates with 4–100 ethylene oxide groups per octylphenol molecule.
6. Alkanolamides in which the carbon chain includes a $C_6$–$C_{18}$ fatty acid reacted with monoethanolamine, diethanolamine or isopropanolamine.
7. Ethoxylated alkanolamides in which the carbon chain consists of a $C_6$–$C_{18}$ fatty acid reacted with ethylene oxide and monoethanolamine, diethanolamine or isopropanolamine.
8. Amine oxides having a carbon chain from $C_6$ to $C_{18}$.
9. Fatty acid ethoxylates with 2–40 ethylene oxide groups per fatty acid molecule where the fatty acid has a carbon chain from $C_4$ to $C_{18}$.
10. Ethylene oxide/propylene oxide (eo/po) block copolymers with average molecular weights of between 500 and 15,000.
11. Nonylphenol ethoxylate propoxylates with average molecular weights between 400–8000.
12. Alkylaryl polyether alcohols prepared by reacting octylphenol with ethylene oxide, e.g., octylphenoxypolyethoxyethanol with between about 1–70, 7–40, 9–30, or 9–10 ethylene oxide groups per molecule, e.g., Triton X-100 (Van Waters and Rogers).
13. Linear alcohol alkoxylates (e.g., ethoxylates, propoxylates) with average molecular weights between 400–8000 and carbon chains from $C_8$ to $C_{18}$.

Anionic surfactants which could be included in the present invention include, but are not limited to, the following examples.

1. Alkyl sulfonate salts and alkylaryl sulfonate salts supplied with sodium, potassium, ammonium, protonated monoethanolamine, diethanolamine, or triethanolamine or protonated isopropanolamine cations, such as the following salts.
   a. Linear primary $C_6$–$C_{18}$ sulfonate salts.
   b. Linear secondary $C_3$–$C_{18}$ sulfonate salts.
   c. Alpha olefin sulfonate salts.
   d. Dodecylbenzene sulfonate salts.
   e. Tridecylbenzene sulfonate salts.
   f. Xylene sulfonate salts.
   g. Cumene sulfonate salts.
   h. Toluene sulfonate salts.
2. Alkyl sulfate salts and alkylaryl sulfate salts supplied with Na, K, $NH_4$, protonated monoethanolamine, diethanolamine, or triethanolamine, or protonated isopropanolamine cations, such as the following salts.
   a. Linear primary $C_6$–$C_{18}$ sulfate salts.
   b. Linear secondary $C_3$–$C_{18}$ sulfate salts.
   c. $C_{12}$–$C_{13}$ benzene sulfate salts.
3. Alkyl $C_6$–$C_{18}$ naphthalene sulfonate salts with Na, K or $NH_4$ cations.
4. Alkyl $C_6$–$C_{18}$ diphenyl sulfonate salts with Na, K or $NH_4$ cations.
5. Alkyl ether sulfate salts or alkylaryl ether sulfate salts supplied with Na, K, $NH_4$, protonated monoethanolamine, diethanolamine, or triethanolamine, or protonated isoprponolamine cations, such as the following salts.
   a. Alkyl $C_8$–$C_{18}$ alcohol (ethoxylate)$_{1-6}$ sulfate salts.
   b. Alkyl $C_8$–$C_{12}$ phenoxy (ethoxylate)$_{1-12}$ sulfate salts.
6. Alkyl ether sulfonate salts or alkylaryl ether sulfonate salts supplied with Na, K, $NH_4$, protonated monoethanolamine, diethanolamine or triethanolamine or protonated isopropanolamine cations, such as the following salts.
   a. Alkyl $C_8$–$C_{18}$ alcohol (ethoxylate)$_{1-6}$ sulfonate salts.
   b. Alkyl $C_8$–$C_{12}$ phenoxy (ethoxylate)$_{1-12}$ sulfonate salts.
7. $C_4$–$C_{18}$ dialkyl sulfosuccinate salts supplied with Na, K, $NH_4$, protonated monoethanolamine, diethanolamine, or triethanolamine or protonated isopropanolamine cations, such as disodium dioctyl sulfosuccinate.
8. Other anionic surfactants such as monoalkyl phosphate ester salts, dialkyl phosphate ester salts, isothionates, or taurate salts.

Cationic surfactants can also be used in the present composition. By way of illustration and not limitation, suitable cationic surfactants may include quaternary ammonium compounds selected from mono $C_6$–$C_{16}$, $C_6$–$C_{10}$ N-alkyl, or alkenyl ammonium surfactants, wherein the remaining N positions are substituted by methyl, hydroxyethyl or hydroxypropyl groups.

Surfactants may be present in the present formulation in concentrations of between about 0.010% and 5%, 0.015% and 2.5%, 0.020% and 1%, or any range subsumed therein.

Adsorbing Agent

The odor-adsorbing agent of this invention may have a particle size range sufficiently small to be suspended easily and to pass through spray dispensers. One method of making a suitable activated carbon is to carbonize a starting material (e.g., coconut shells, coal, wood, soybean hulls, almond hulls, hazel nut shells, black walnut shells, Brazil nut shells, macadamia nut shells) at a high temperature in an inert atmosphere. The carbonized coconut shells are then steam activated at 800° C. to 1000° C. In many cases, the foregoing produces activated carbon with an internal surface area of from 900 square meters per gram to 1500 square meters per gram. Suitable activated carbons include those sold as 208C 4×8, 607 4×6, HR5 12×40, HR5 AW 12×40, 206A 12×40, 207A 4×10, and 207AW 12.40 (Barnebey and Sutcliffe). However, other adsorbents which might be suitable in mixtures with the foregoing or as sole adsorbents include modified clay media (e.g., 30% organically modified bentonite clay and 70% anthracite or activated carbon), bone char adsorbent, and impregnated activated carbon. If used in the present formulation, activated carbon may be present in an amount of about 1.0% or 1.5% or in amounts between about 0.10% and 5%, 0.20% and 2.5%, 0.70% and 2.00%, or any range subsumed therein.

Alkali Metal Carbonates/Bicarbonates

The alkali metal carbonate or bicarbonate used in the present formulation may be effective in suppressing and/or adsorbing odors and scents. Suitable alkali metal salts of this nature include sodium and potassium carbonates and bicarbonates and be present in amounts between about 0.01% and 5%, 1% and 5%, 2% and 4%, or any range subsumed therein.

Base

A base, such as an alkali metal hydroxide (e.g., Na OH) may be present in the formulation of this invention. The base will adjust the pH of the present formulation to between about 7 and 13, 8 and 12, 9 and 11, or any pH at which the present formulation disperses on textiles and effectively adsorbs and/or prevents the wearer's scent or odors from emanating therefrom. Thus, in some embodiments the base may be present in an amount between about 0.1% and 5.0%, 0.2% and 2.5%, 0.25% and 1.0%, or any range subsumed therein.

One way of making the present formulation is to add the preservatives, alkali metal carbonate or bicarbonate, surfactants, and base (if present) to a predetermined volume of water (e.g., deionized). The foregoing ingredients may be mixed or agitated until they are either in solution or emulsified. Undissolved ingredients and particulate impurities may then be removed by passing the solution through one or more filters (e.g., 10, 5, 1 micron). Finally, the odor-adsorbing agent is added and suspended (e.g., by agitation). Optionally, a dye may be added to the solution before or after the filtration step. A suitable black dye may be obtained from Keystone Corporation. The dye may be present in an amount such that the present formulation can be detected when applied to textiles, e.g., 0.01% –1.0%, or any range subsumed therein.

When being used, the present formulation may be agitated to the extent necessary to resuspend any settled activated carbon particulates. The present formulation may be applied as a spray or mist application to any desired surface. From four to five ounces of the present solution can be spray-applied to an individual garment. Alternatively, 128 (±4) ounces can be applied to a garment dipped in the present solution. For example, the present formulation may be sprayed on apparel such as clothing and boots, or on hunting gear and equipment. When applied thusly, the solution permeates the fibers and/or pores of the clothing, boots, and equipment. The solution may also be applied to the surfaces of equipment made of wood, metal, plastic, and composites. Moreover, the present formulation may be applied by immersing the article therein. After being applied, the solution dries and is actively present on the surface until washed or worn away. The present formulation may be applied as frequently as desired during use.

EXAMPLE I

Samples of 1) a test scent blocking formulation of the present invention (denoted below as A) and 2) a test scent blocking formulation of the prior art (denoted below as B) were tested for sorption capacity. The test scent blocking formulations had the ingredients shown below in Table 1.

TABLE 1

Ingredients Present in Test Scent Blocking Formulations of the Present Invention (A) and the Prior Art (B).

|  | A (%) | B (%) |
|---|---|---|
| Deionized water | 96.036 | 96.591 |
| Sodium bicarbonate[1] | 2.000 | 3.000 |
| Sodium hydroxide | 0.189 | 0.189 |
| Sodium propionate | 0.050 | 0.050 |
| Triton X 100 ® | 0.025 | 0.020 |
| Particulate activated carbon[2] | 1.500 | — |
| Glydant Plus ® | 0.200 | 0.150 |

[1]pH 9–11.
[2]Minimum adsorption capacity 60% (w/w); particle size (powder) 325xF; minimum mean particle diameter 18 microns; maximum mean particle diameter 62 microns; D(90) micron particle size below which 90% of particles flow = 165 maximum; derived from coconut shells.

Two sets of test "spike" solutions were prepared at various levels in a 1% Triton×100 aqueous solvent using compounds chosen from prior studies as associated with human odors. A first set of spike solutions contained known concentrations of butyric acid and isovaleric acid. Butyric and isovaleric acids are known to be present in human perspiration. ("Study of the Composition of Volatile Compounds of Human Sweat and Urine," Savina et al., Kosm. Biol. Aviakosm. Med., 1975). A second set of spike solutions contained known concentrations of six non-acidic organic compounds. These non-acidic compounds were chosen for their chemical functionality and/or their documented presence in human perspiration or urine. The six compounds and their functional classes were an aldehyde, isovaleraldehyde (3-methylbutanal); an alcohol, 2-butanol; a ketone, 2-hexanone; an ester, ethylbutyrate (ethyl butanoate); a disulfide, dimethyl disulfide (2,3-dithiabutane); and an unsaturated hydrocarbon limonene (methyl-4-isopropenyl-1-cyclohexene). Aldehydes, alcohols, and ketones and acids are known to occur in human perspiration and urine. The ester, unsaturated hydrocarbon, and disulfide are also commonly found in various human use products.

Three pieces of 70 mm diameter filter paper (Whatman GF/A 41) were inserted into, then formed to cover the sides of, 40 mm VOA vials. The VOA vials with inserted filter papers were then dried for two hours at 85° C. The vials with dried filter papers and septum screw caps were weighed. The test scent blocking formulations were thoroughly shaken to mix them well before being added to two ml vials. The two ml vials were then rolled to coat the formulation evenly on the filter papers. The total volume of test scent blocking formulation dispensed into each two ml vial was held constant at 30 ul of total solution by adding 1% Triton×100 throughout the sampling period as necessary. This ensured that the test formulation did not splash onto the filter paper and also minimized solvent effects in the system. The VOA vial was then sealed with a septum screw cap and allowed to stand for two hours at room temperature. The two hour period was to attain equilibrium with respect to vapor and liquid phases of the spike solution. After the two hour period, a 75 um Carboxen/PDMS solid phase micro extraction fiber (SPME fiber), available from Supelco as part # 57318, was inserted through the septum of the cap and the headspace in the VOA vial was extracted for 30 minutes at room temperature. Following the SPME extraction, the SPME fiber was desorbed into a gas chromatography-mass spectrometry system (GCMS) and analyzed under the select ion monitoring (SIM).

The SPME fiber was then removed from the vial headspace, inserted into a GC injection port, and desorbed in the GC injection port for three minutes at 280° C. The following conditions were present with respect to the GCMS instrument:

| | |
|---|---|
| Interface Temperature | 280° C. |
| Source Temperature | 200° C. |
| Injector Temperature | 280° C. |
| Initial Temperature | 30° C. |
| Initial Hold | 3 min. |
| Ramp Rate | 6° C./min to 90° C., 20° C./min to 230° C., hold 3 min |
| Column | DB Wax (J&W, 30 m × 0.25 mm × 0.25 um). |
| Mass Range | SIM (Select Ion Monitoring) |
| Solvent Delay | 3.2 min |
| Group 1 Start Time (mass, dwell) | 3.2 min<br>44, 100<br>58, 100 |
| Group 2 Start Time (mass, dwell) | 6.0 min<br>45, 100<br>59, 100<br>71, 100<br>88, 100 |
| Group 3 Start Time (mass, dwell) | 7.2 min<br>43, 100<br>58, 100<br>79, 100<br>94, 100 |
| Group 4 Start Time (mass, dwell) | 8.2 min<br>68, 100<br>93, 100 |
| Group 5 Start Time (mass, dwell) | 11.5 min<br>60, 100<br>73, 100<br>87, 100 |
| Group 6 Start Time | 21.7 min<br>200, 100 |

Individual compound response factors were generated daily from at least a two point standard curve. The two point standard curve bounded the response of the compounds in the headspace of the VOA vial. Standards used were prepared by adding a known mass of the analytes to a blank VOA vial, extracting the headspace with the SPME fiber for 30 minutes, and analyzing desorbed standards under the same GCMS method used to analyze the samples. The daily response factors (area of the principal ion vs. mass of analytes added to a 40 ml VOA vial) were stored in a calibration file and were used to calculate the headspace concentration from the testing done in a given day.

Each formulation sample was prepared and analyzed at least three times. Concentrations of analytes remaining in the headspaces were calculated by applying the response factors generated the same day as the test was conducted. A blank vial containing only the dried filter paper and 30 ul of the Triton×100 without analytes was shown to be free of interferences. The mass of each test compound sorbed by each treatment solution was calculated by the following equation:

Mass Sorbed=Mass Added by Spike−Mass Remaining in Headspace.

The analysis protocol was based on about 0.1 to 1.0 ug of each analyte remaining in the headspace after being sorbed for two hours (5–15 ug acids remaining). In order to achieve this endpoint, the mass of each non-acid analyte added to the closed systems was about 1 ug for the second scent blocking formulation (Table 2). In the case of the present sent blocking formulation, several hundreds of micrograms were added. The amount of the two acids was held constant at about 69 ug for each scent blocking solution because the sorption/neutralization capacity of each formulation for the acids was substantially the same.

TABLE 2

Mass (ug) of Analytes Added to Two Scent Blocking Solutions.

| | A | B |
|---|---|---|
| Isovaleraldehyde | 275 | 0.66 |
| 2-butanol | 415 | 1.00 |
| Ethylbutyrate | 333 | 0.80 |
| Dimethyl disulfide | 354 | 0.85 |
| 2-hexanone | 320 | 0.77 |
| d-limonene | 303 | 0.73 |
| Butyric acid | 68.7 | 68.7 |
| Isovaleric acid | 69.6 | 69.6 |

The sorption capacity results by individual compound (mean±standard deviation) are depicted in Table 3. Considering the capacity for all compounds spiked, the present formulation had about 15 times more capacity than the prior art formulation. Because the acid sorbing capacity was the same for both scent blocking solutions, the addition of activated charcoal was obviously the reason for the superior sorbing of the non-acid compounds by the present formulation A. Considering only the six non-acid compounds, the present formulation had about 1000 fold more sorption capacity than the prior art formulation.

TABLE 3

Mean Sorption Capacity of Two Scent Blocking Solutions

| Analyte | A | B |
|---|---|---|
| Isovaleraldehyde | 274 (0.1) | 0.1 (0.1) |
| 2-butanol | 413 (0.6) | 0.7 (<0.1) |
| Ethylbutyrate | 333 (<0.1) | 0.5 (<0.1) |
| Dimethyl disulfide | 354 (0.1) | <0.1 (0.1) |
| 2-hexanone | 319 (<0.1) | 0.4 (0.1) |
| d-limonene | 303 (0.1) | 0.4 (0.1) |
| Butyric acid | 66 (2.9) | 66 (2.8) |
| Isovaleric acid | 66 (2.9) | 67 (2.7) |
| Total All Compounds | 2128 | 135 |
| Total Non-Acids | 1996 | 2.1 |

Four additional embodiments of the present odor inhibiting formulation are presented below in Table 7 as formulations C, D, E, and F.

TABLE 7

Ingredients Present in Test Scent Blocking Formulations of the Present Invention.

| | E (%) | F (%) | G (%) | H (%) |
|---|---|---|---|---|
| Deionized water | 95.500 | 95.050 | 92.500 | 96.675 |
| Sodium bicarbonate | | 0.850 | 1.750 | 2.500 |
| Potassium carbonate | | | 1.000 | |
| Sodium hydroxide[1] | 2.500 | 1.500 | 2.000 | |
| Sodium Propionate | | 0.050 | | 0.075 |
| Glydant Plus ® | | | 0.250 | |
| Triton X 100 ® | | 1.050 | | |
| Particulate activated carbon[2] | 2.000 | 1.500 | 2.500 | 0.750 |

[1]pH 9–11.
[2]HR5 AW 12x40 (Barneby and Sutcliffe).

Because numerous modifications of this invention may be made without departing from the spirit thereof, the scope of the invention is not to be limited to the embodiments illustrated and described. Rather, the scope of the invention is to be determined by the appended claims and their equivalents.

What is claimed is:

1. A substantially liquid formulation for application to apparel, said formulation minimizing scents emanating from persons attired in the apparel, said formulation comprising:
    between about 0.01% and 5.0% by weight of an alkali metal carbonate salt or an alkali metal bicarbonate salt;
    between about 0.01% and 5.0% by weight of a surfactant;
    between about 0.025% and 5.0% by weight of a preservative comprising an antimicrobial formulation; and
    about 0.10% and 5.0% by weight of an odor sorbing agent consisting essentially of activated carbon.

2. The formulation of claim 1, in which the surfactant is a nonionic surfactant, an anionic surfactant or a cationic surfactant.

3. The formulation of claim 1, in which the surfactant comprises a nonionic surfactant.

4. The formulation of claim 3, in which the nonionic surfactant comprises an alkylaryl polyether alcohol.

5. The formulation of claim 4, in which the alkylaryl polyether alcohol includes between about 9 and 30 ethylene oxide groups per molecule.

6. The formulation of claim 1, the preservative including an alkali metal salt of a $C_2$–$C_6$ carboxylic acid.

7. The formulation of claim 1, the preservative including an aldehyde or an aldehyde derivative.

8. The formulation of claim 1, the preservative including a diazolidinyl urea.

9. The formulation of claim 1, the preservative including an imidazolidinyl urea.

10. The formulation of claim 1, in which an alkali metal bicarbonate salt is present.

11. The formulation of claim 1, in which a pH of the formulation is between 7 and 13.

12. The formulation of claim 1, in which a pH of the formulation is between 9 and 11.

13. The formulation of claim 1, further comprising an alkali metal hydroxide in an amount such that a pH of the formulation is between about 7 and 13.

14. The formulation of claim 1, further comprising an alkali metal hydroxide in an amount such that a pH of the formulation is between 9 and 11.

15. A method of making a substantially liquid formulation for surface application to an article of apparel, said formulation absorbing scents of persons attired in the apparel, said method comprising:
    forming an aqueous solution of between about 0.01% and 5.0% by weight of an alkali metal carbonate salt or an alkali metal bicarbonate salt;

adding between about 0.025% and 5.0% by weight of a preservative to the aqueous solution;

adding between about 0.01% and 5.0% by weight of a surfactant; and suspending between about 0.1% and 5.0% by weight of a particulate odor-sorbing agent consisting essentially of activated carbon in the aqueous solution.

16. The method of claim 15, in which the aqueous solution is formed with an alkali metal bicarbonate.

17. The method of claim 15, in which the added preservative comprises an antimicrobial formulation.

18. The method of claim 15, in which the added preservative comprises an alkali salt of a $C_2$–$C_6$ carboxylic acid.

19. The method of claim 15, in which the added preservative comprises an aldehyde or aldehyde derivative.

20. The method of claim 15, in which the added preservative comprises a hydantoin or hydantoin derivative.

21. The method of claim 15, in which the added preservative comprises a mixture of diazolidinyl urea and an esterified phenol or an esterified phenol derivative.

22. The method of claim 15, in which the added preservative comprises an imidazolidinyl urea.

23. The method of claim 15, further comprising adding an alkali metal hydroxide such that the pH of said substantially liquid formulation is between about 7.0 and 13.0.

24. The method of claim 15, further comprising adding an amount of an alkali metal hydroxide such that a pH of the formulation is between about 9 and 11.

25. The method of claim 15, in which the added surfactant is a nonionic surfactant an anionic surfactant or a cationic surfactant.

26. The method of claim 15, in which the added surfactant comprises a nonionic surfactant.

27. The method of claim 15, in which the added surfactant comprises an alkylaryl polyether alcohol.

28. The method of claim 15, in which the added surfactant comprises an alkylaryl polyether alcohol with between about 9–10 ethylene oxide groups per molecule.

29. An aqueous formulation for surface application to apparel, said formulation minimizing scents emanating from persons attired in the apparel, said formulation consisting essentially of:

between about 0.01% and 5.0% by weight of a water soluble alkali metal carbonate or a water soluble alkali metal bicarbonate, between about 0.025% and 5.0% by weight of a preservative, between about 0.01% and 5.0% by weight of activated carbon;

and optionally between about 0.01% and 5.0% by weight of a surfactant.

30. The formulation of claim 29, in which the water soluble salt is an alkali metal bicarbonate.

31. The formulation of claim 29, in which the water soluble salt is sodium bicarbonate.

32. The formulation of claim 29, in which between 0.1 weight percent and 5.0 weight percent activated carbon is present.

33. The formulation of claim 29, the surfactant comprising a nonionic surfactant.

34. The formulation of claim 33, the nonionic surfactant comprising an alkylaryl polyether alcohol.

35. The formulation of claim 34, the alkylaryl polyether alcohol including between about 9 and 30 ethylene oxide groups per molecule.

36. The formulation of claim 29, the preservative including an antimicrobial formulation.

37. The formulation of claim 29, the preservative including an alkali metal salt of a $C_2$–$C_6$ carboxylic acid.

38. The formulation of claim 29, the preservative including sodium propionate.

39. The formulation of claim 29, the preservative including a compound selected from an aldehyde, an aldehyde derivative, a diazolidinyl urea, an imidazolidinyl urea.

40. The formulation of claim 29, in which a formulation pH is between about 7 and 13.

41. The formulation of claim 29, in which a formulation pH is between about 9 and 11.

42. The formulation of claim 29, further comprising an alkali metal hydroxide in an amount such that a pH of said formulation is between about 7 and 13.

43. The formulation of claim 29, further comprising an alkali metal hydroxide in an amount such that a pH of said formulation is between about 9 and 11.

* * * * *